United States Patent [19]

Trnkoczy et al.

[11] 4,434,798

[45] Mar. 6, 1984

[54] CONTROL CIRCUIT OF A FUNCTIONAL AND THERAPEUTIC STIMULATOR

[75] Inventors: Amadej Trnkoczy; Miha Stopar; Dušan Filipič, all of Ljubljana; Jože Opeka, Vrhika, all of Yugoslavia

[73] Assignee: Gorenje Tovarna Gospodinjske Opreme N.Sol.O. Velenj, Velenje, Yugoslavia

[21] Appl. No.: 314,463

[22] Filed: Oct. 23, 1981

[30] Foreign Application Priority Data

Oct. 23, 1980 [YU] Yugoslavia ............................ 2724/80

[51] Int. Cl.³ .............................................. A61N 1/30
[52] U.S. Cl. .................................................. 128/421
[58] Field of Search ................... 128/420 R, 421, 422, 128/423 R

[56] References Cited

U.S. PATENT DOCUMENTS

| 3,294,092 | 12/1966 | Landauer | 128/420 R |
| 3,718,132 | 2/1973 | Holt et al. | 128/421 |
| 4,033,356 | 7/1977 | Hara | 128/422 |
| 4,177,819 | 12/1979 | Kofsky et al. | 128/422 |

Primary Examiner—William E. Kamm
Attorney, Agent, or Firm—Fleit, Jacobson, Cohn & Price

[57] ABSTRACT

In the control circuit of a functional and therapeutic stimulator with which pulses are generated for an artificial provocation of muscle contraction, the amplitude thereof and thereby the intensity of contractions can be regulated in dependence upon the positional pick-up. With the aid of a control signal an automatic switching in of the circuit is attained, whereat the circuit can be operated in a proportional or cyclic mode.

3 Claims, 1 Drawing Figure

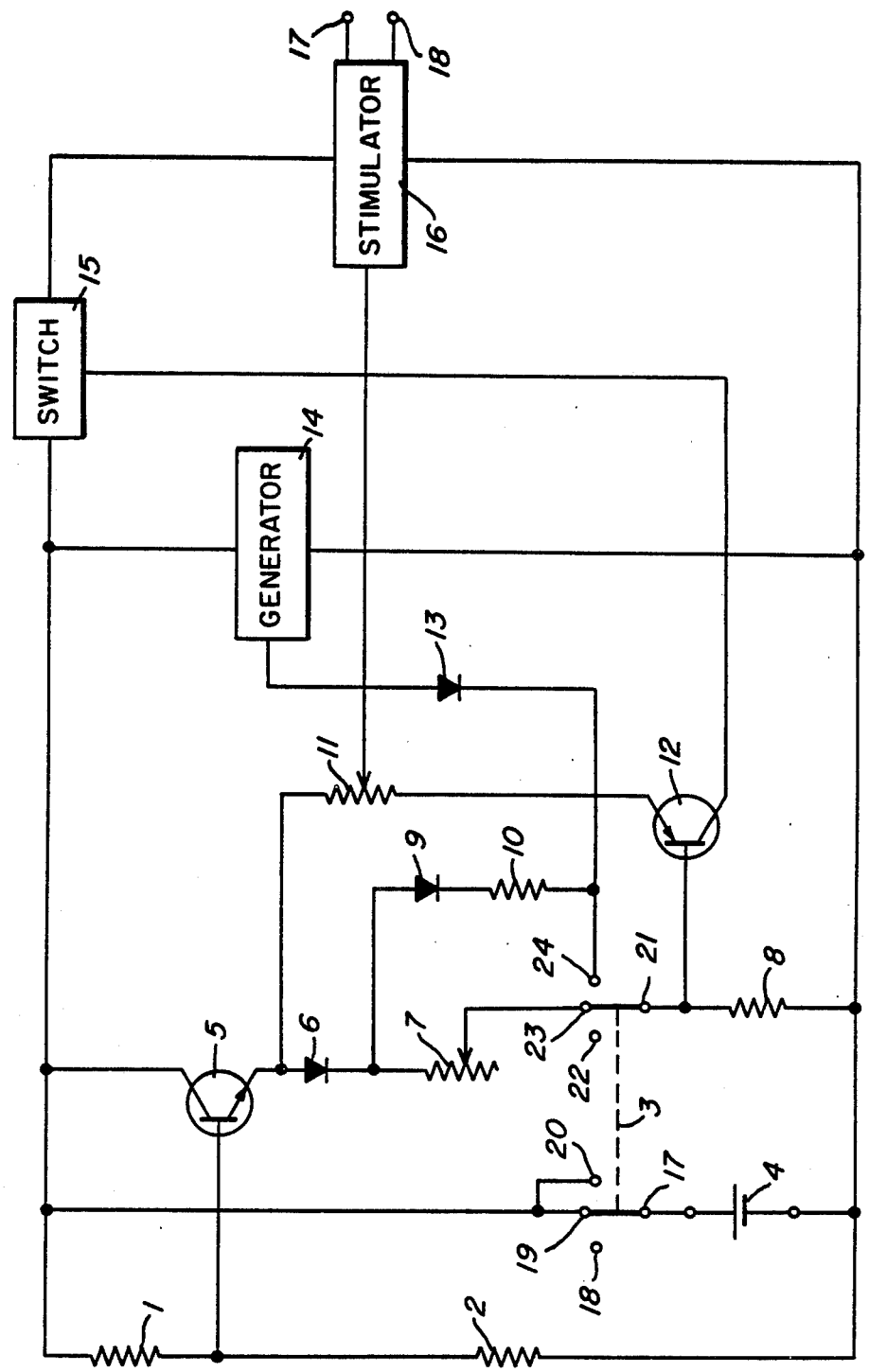

CONTROL CIRCUIT OF A FUNCTIONAL AND THERAPEUTIC STIMULATOR

BACKGROUND OF THE INVENTION

Object of the invention is a control circuit of a functional and therapeutic stimulator which enables proportional regulation of the amplitude of stimulation pulses and thereby the intensity of the artificially provoked muscle contractions in dependence upon the position of the positional pick-up, and an automatic switching in of the electronic circuit of the stimulator with the aid of the control signal.

Known embodiments of control circuits of the kind are either limited in the manner of operation thereof, or they do not possess the technical performances of the novel circuit. The positional pick-up for the control signal is mostly fixed with tapes onto the patient's back so that a hemiplegic patient cannot fix it on his back himself.

The prior art embodiment of the control circuit of a functional and therapeutic stimulator has some drawbacks. A very complicated and expensive positional pick-up with a microswitch was built into the circuit, which caused undesired stimulation pulses at switching off the stimulator. Another drawack lies in the nonlinearity of the characteristics of the amplitude adjustment.

The aim of the invention is to provide a control circuit of a functional and therapeutic stimulator which enables a proportional regulation of stimulation pulses and automatic switching-on of the electronic circuit of the stimulator. The stimulator contains a simple electronic circuit with minimum current consumption, the pick-up of the control signal being physically built into the stimulator. The stimulator can be positioned simply, its casing being an industrial design.

The aim as set forth was attained by an electronic circuit shown in the accompanying drawing, and by a special connection of the positional pick-up.

BRIEF DESCRIPTION OF DRAWINGS

The sole FIGURE depicts an electrical circuit diagram of a preferred embodiment of the functional and therapeutic stimulator.

In the circuit according to the invention, the base of the transistor 5 couples the resistor 1 connected to one pole of the battery supply 4 and over the resistor 2 connected to the second pole of the battery supply 4. The collector of the transistor 5 couples contacts 19 and 20 of the switch 5 connected to one pole of the battery supply 4, the emitter being couples to the diode 6 connected to the first contact of rheostat potentiometer 7. The sliding contact of rheostat 7 is connected to the contact 23 of the switch 3. The contact 21 of the switch 3 is connected to the base of the transistor 12 and over the resistor 8 and to the second pole of the battery supply 4. The emitter of the transistor 12 is connected to the second contact of the potentiometer 11, the first contact of which is connected to the emitter of the transistor 5. The collector of the transistor 12 is connected to the electric switch 15. The output of the generator 14 of the stimulation pulse groups couples the diode 13 connected to the contact 24 of the switch 3, the same contact being connected to the resistor 10 and the diode 9 connected to the first contact of the rheostat 7.

The switch 3 performs three functions. It switches off the electronic circuit when the switching contacts 17 and 21 are in the position 18 and 22. In this case one pole of the battery supply 4 is switched off. The switch 3 in the position 19 connects one pole of the battery supply 4 to the electric circuit and connects the sliding contact of the rheostat 7 to the base of the transistor 12. The electronic circuit operates in a proportional operation method. Cyclic operation is attained by switching over the contacts 17 and 21 of the switch 3 into the position 20 and 24. Over the contact 20 of the switch 3 one pole of the battery supply 4 is connected to the electronic circuit, whereat the base of the transistor 12 is connected to the output of the stimulation pulse group generator 14 through the contact 24 of the switch 3 and the diode 13.

The sliding contact of the potentiometer 11 is connected to the input of the functional and therapeutic stimulator 16.

The control electronic circuit of the functional and therapeutic stimulator according to the invention operates in the following manner:

(a) Proportional Operation

Contacts of the switch 3 are in the following position: 17 on 19 and 21 on 23. One pole of the battery supply 4 is connected to the circuit. The transistor 5 is connected as an emitter follower and has a constant base voltage which is defined by the resistors 1 and 2. Into the emitter branch of the transistor 5 there is connected the rheostat 7, the sliding contact of which is connected to the switch 3 and resistor 8 which is connected to the second pole of the battery supply 4. By varying the resistance of the rheostat 7, the current changes, and thereby the voltage changes on the base of the transistor 12, which is connected as an emitter follower like the transistor 5. The emitter of the transistor 12 connects to the potentiometer 11 which is connected to the emitter of the transistor 5. When the sliding contact of the rheostat 7 is on its first contact (resistance $\phi$), the first and the second contact of the potentiometer 11 have to be on the same voltage potential. By raising the resistance of the rheostat 7 (the sliding contact moves away from the first contact), the voltage on the base of the transistor 12 drops, which is also followed by the voltage on the second contact of the potentiometer 11. A voltage difference arises between the first and the second contact of the potentiometer 11, which is transferred to the sliding contact to the input of the functional and therapeutic stimulator. The potentiometer 11 is a voltage divider; by moving the sliding contact from the first to the second contact, the voltage level is regulated, which is picked up from the potentiometer. Upon this voltage there is proportionally dependent the amplitude of the stimulation pulses on the output of the functional and therapeutic stimulator. This means that the slope of the dependence of the stimulation pulses amplitude upon the position of the rheostat 7 is changed by the potentiometer 11.

The resistance layer of the rheostat 7 has a length of some millimeters whereof the starting millimeters are used for the switching on of the electronic switch 15. A minimum change of the position of the sliding contact of the rheostat 7 causes such a change of the voltage on the base of transistor 12 that it switches on the electric switch 15 which subsequently connects all larger consumers of the electric current to one pole of the battery supply 4. Thereby the consumption of the electric energy is substantially reduced. The remaining sliding space of the sliding rheostat 7 is used as a positional pick-up for the proportional control of the output stimulation voltage.

(b) Cyclic Operation

Contacts of the switch 3 are in the following position: 17 on 20 and 21 on 24. The transistor 3 operates as an emitter follower and has a constant emitter voltage. Over the diodes 6 and 9 and the resistor 10 it is connected to the base of the transistor 12. The stimulation pulse group generator 14 connects to the diode 13 which is connected to the base of the transistor 12. When the output of the generator 14 is on the level "1" (one pole of the battery supply 4), the base of the transistor 12 is practically the same potential as the first pole of the battery supply 4, and the electric valve 15 which is controlled by the transistor 12 is closed. The functional and therapeutic stimulator is out of operation. When the voltage level at the output of the stimulation pulse group generator 14 is "0" (the second pole of the battery supply), it has no influence upon the base of transistor 12 because of the diode 13, which represents a barrier for the level "0". The base of the transistor 12 is at a voltage potential which is lower than the voltage at the emitter of the transistor 5 for the voltage drop on the diode 9 and resistor 10. The resistor 10 is selected in such manner that such a drop appears across the resistor and the diode as would, at proportional operation, be caused at sliding contact of the rheostat pulled to the end. Between the first and the second contact of the potentiometer 11 there exists a voltage difference which is led to the input of the functional and therapeutic stimulator through the sliding contact. Upon this voltage there is proportionally dependent the amplitude of the stimulation pulses. The stimulator operates in a cyclic manner: stimulation, interval etc. This operation manner is used for therapeutic purposes.

What is claimed is:

1. A control circuit for a functional and therapeutic stimulator that produces output pulses, which control circuit comprises a battery, switching means for connecting said battery to the circuit and for selecting between proportional and cyclic modes of operation of the stimulator, a first control means for adjusting the relative amplitude of the output pulse of the stimulator, a second control means for adjusting the absolute amplitude of the output pulse of the stimulator, a pulse group generator for defining the length of pulse groups of the stimulator in the cyclic mode of operation, and an electronic switching means for switching on the stimulator.

2. A control circuit for a functional and therapeutic stimulator comprising a double-pole three-throw switch having a movable arm, a battery, an electronic switch, a voltage divider constituted by two resistors, a first transistor, a first diode, a potentiometer, a rheostat, and a second transistor wherein a first movable arm of the double-pole three-throw switch in a second and third position connectes a first pole of said battery to the electronic switch to one end of the voltage divider, the connecting point thereof being connected to the base of the first transistor and the other end thereof being connected to the second pole of said battery and to the collector of the first transistor, the emitter of which is connected to the first diode and to one end of the potentiometer for adjusting the absolute value of the output pulse of the stimulator, the other end of said first diode being connected to one end of a rheostat for adjusting the relative amplitude of output pulse of the stimulator, the other end of the rheostat being during the proportional mode of operation connected to the base of a second transistor through a resistor which is connected to the second pole of said battery, whereby the emitter of said second transistor is connected to the other end of said potentiometer for adjusting the absolute amplitude of the output pulse of the stimulator, a sliding contact of the potentiometer being connected to a control input of the stimulator and the collector of said second transistor being connected to the control input of said electronic switch, the output of which is connected to the power input of the stimulator.

3. A control circuit of a functional and therapeutic stimulator a pulse group generator wherein a first movable arm of the double-pole three-throw switch in a second and third position connects the first pole of said battery to the electronic switch to one end of the voltage divider, the connecting point thereof being connected to the base of the first transistor and the other end being connected to the second pole of said battery and to the collector of the first transistor, the emitter of which is connected to the first diode and to one end of the potentiometer for adjusting the absolute value of the output pulse of the stimulator, the other end of said first diode being used during a cyclic mode of operation and being connected to one end of a second diode, the other end of which being connected to a resistor which also is to the base of a second transistor, which is connected to a resistor connected to the second pole of said battery and through a diode connected to the control input of the pulse group generator, whereby the emitter of said second transistor is connected to the other end of said potentiometer for adjusting the absolute value of the output pulse of the stimulator, a sliding contact of the potentiometer being connected to the control input of the stimulator and the collector of said second transistor being connected to the control input of said electronic switch, the output of which is connected to the power input of the stimulator.

* * * * *